United States Patent
Ferritto et al.

(10) Patent No.: US 6,653,378 B2
(45) Date of Patent: Nov. 25, 2003

(54) SILICONE ELASTOMER COMPOSITIONS

(75) Inventors: Michael Salvatore Ferritto, Midland, MI (US); Zuchen Lin, Midland, MI (US); William James Schulz, Jr., Midland, MI (US); Janet Mary Smith, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/020,612

(22) Filed: Dec. 13, 2001

(65) Prior Publication Data

US 2002/0086935 A1 Jul. 4, 2002

Related U.S. Application Data

(60) Provisional application No. 60/256,533, filed on Dec. 18, 2000.

(51) Int. Cl.[7] .................... C08G 77/22; C08G 77/38; C03K 5/54
(52) U.S. Cl. ................ 524/267; 528/26; 528/27; 528/28; 528/29; 528/38; 524/268
(58) Field of Search ............... 528/25–29, 38; 524/267, 268

(56) References Cited

U.S. PATENT DOCUMENTS

| | | | | |
|---|---|---|---|---|
| 2,819,245 A | * | 1/1958 | Shorr .................. | 528/27 |
| 3,655,420 A | * | 4/1972 | Tichenor .............. | 428/391 |
| 4,359,545 A | * | 11/1982 | Ona et al. ............ | 252/8.61 |
| 4,584,342 A | * | 4/1986 | Kondow .............. | 524/860 |
| 4,954,590 A | * | 9/1990 | Yoshida et al. ....... | 526/259 |
| 4,987,169 A | | 1/1991 | Kuwata et al. ........ | 524/267 |
| 5,760,116 A | | 6/1998 | Kilgour et al. ........ | 524/268 |
| 5,811,487 A | | 9/1998 | Schulz, Jr. et al. .... | 524/862 |
| 5,889,108 A | | 3/1999 | Zhang ................ | 524/862 |
| 5,895,794 A | * | 4/1999 | Berg et al. ............ | 523/217 |
| 5,948,855 A | | 9/1999 | Lin et al. ............. | 524/837 |
| 6,238,657 B1 | | 5/2001 | Lin et al. ............. | 424/70.12 |
| 6,515,094 B2 | * | 2/2003 | Czech et al. .......... | 528/12 |

FOREIGN PATENT DOCUMENTS

| | | | | |
|---|---|---|---|---|
| DE | 19957324 | 5/2001 | ......... | C09D/183/04 |
| EP | 0739928 | 10/1996 | ......... | C08J/3/03 |
| EP | 0893467 | 1/1999 | ......... | C08J/3/03 |
| EP | 0894840 | 2/1999 | ......... | C09D/183/08 |
| EP | 1048686 | 11/2000 | ......... | C08G/77/46 |
| WO | WO 95/35183 | 12/1995 | ......... | B23K/20/12 |

* cited by examiner

Primary Examiner—Robert Dawson
Assistant Examiner—Marc S Zimmer
(74) Attorney, Agent, or Firm—Sharon K. Severance; Alan Zombeck

(57) ABSTRACT

This invention related to silicone elastomer compositions in the form of gels and/or organized structures. The silicone elastomer compositions are produced by reacting a siloxane having a first reactive group with a crosslinker having a second reactive group in a diluent. One reactive group is selected from epoxy-functional groups or chlorohydrin functional groups while the other reactive group is a functional group that reacts with epoxy-functional groups or chlorohydrin functional groups (i.e. amine, hydroxyl). The silicone elastomer compositions of the instant invention are particularly useful in personal care products, textiles, auto care products, and laundry products and for the delivery of active ingredients.

20 Claims, No Drawings

SILICONE ELASTOMER COMPOSITIONS

This application claims the benefit of U.S. Provisional Application No. 60/256,533 filed Dec. 18, 2000.

FIELD OF THE INVENTION

This invention relates to silicone elastomer compositions in the form of gels and/or organized structures.

BACKGROUND OF THE INVENTION

In personal care formulations it has become desirable to use low viscosity silicones to impart a number of benefits to the formulation. However, because of the addition of the low viscosity silicone, there must be additionally added a thickener to the personal care formulation. Certain silicone polymers have found utility as the thickening agent because they can be used in the quantities necessary to thicken the composition without degrading the properties of the personal care formulation. Typically, the silicone polymer and low viscosity silicone are combined to form a paste. This paste can then be used in the personal care formulation. Such silicone polymers are described in U.S. Pat. No. 4,987,169 to Kuwata et al., U.S. Pat. No. 5,760,116 to Kilgour et al., U.S. Pat. No. 5,811,487 to Schulz, Jr. et al. and U.S. Pat. No. 5,889,108 to Zhang and U.S. Pat. No. 6,238,657 to Lin et al.

This invention pertains to functionalized silicone elastomer compositions that are in the form of gels and/or organized structures. These functionalized silicone elastomer compositions are particularly useful in personal care formulations.

SUMMARY OF THE INVENTION

This invention pertains to silicone elastomer compositions that may be in the form of gels and/or organized structures. The silicone elastomers may be produced by reacting (I) 0.1 to 99.89 wt. % based on the weight of all components (i.e. A–C and any optional components) of a siloxane oligomer or polymer having units of

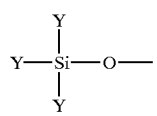

where each Y is independently selected from
  R': an alkyl group with 1 to 30 C atoms, an aryl group having 6 to 15 carbon atoms, an alkaryl group having 6 to 15 carbon atoms, and an aralkyl group having 6 to 15 carbon atoms;
  Z: a reactive group selected from epoxy-functional groups or chlorohydrin functional groups;
  Z': a functional group that reacts with epoxy-functional groups or chlorohydrin functional groups (i.e. amine, hydroxyl);
  F: a functional group other than Z or Z', and
  O (oxygen radicals);
with the proviso that at least 50 mol % of the Y groups in the siloxane are R', preferably methyl and there are at least two Z and/or Z' groups in the siloxane;

(II) 0.1 to 99.89 wt. % based on the weight of all components of a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both,
  further wherein (I), (II) or both (I) and (II) contain at least one F group;
  in (III) 0.1 to 99.89 wt. % based on the weight of all components a diluent selected from (i) water; (ii) a silicone fluid; (iii) a polar organic compound and (iv) a non-polar organic compound and (v) mixtures thereof.

Depending on the diluent (III) selected for the reaction between the siloxane and the crosslinker, the resulting elastomer may be in the form of a gel or organized structure. The elastomers of the instant invention are particularly useful in personal care products, textiles, auto care products, and laundry products and for the delivery of active ingredients.

DETAILED DESCRIPTION OF THE INVENTION

This invention pertains to silicone elastomer compositions that may be in the form of gels or organized structures, for example. The silicone elastomers are produced by reacting (I) 0.1 to 99.89 wt. % based on the weight of all components (i.e. I–III and any optional components) of a siloxane oligomer or polymer having units of

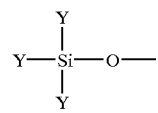

where each Y is independently selected from
  R' is selected from the group consisting of an alkyl group with 1 to 30 C atoms, an aryl group having 6 to 15 carbon atoms, an alkaryl group having 6 to 15 carbon atoms, and an aralkyl group having 6 to 15 carbon atoms;
  Z is selected from epoxy functional groups, chlorohydrin functional groups or mixtures thereof,
  Z' is a functional group that react with epoxy groups or chlorohydrin functional groups (i.e. amine, hydroxyl),
  F is a functional groups other than Z or Z', and
  O (oxygen radicals);
with the proviso that at least 50 mol % of the Y groups in the siloxane are R', preferably methyl and there are at least two Z and/or Z' groups in the siloxane;

(II) 0.1 to 99.89 wt. % based on the weight of all components of a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z, Z' or both,
  further wherein (I), (II) or both (I) and (II) contain at least one F group;
  in (III) 0.1 to 99.89 wt. % based on the weight of all components of a diluent selected from (i) water; (ii) a silicone fluid; (iii) a polar organic compound and (iv) a non-polar organic compound and (v) mixtures thereof.

Depending on the diluent (III) selected the resulting elastomer may be in the form of a gel or organized structure.

By "organized structure" it is meant liquid crystals, vesicles, bi-layers, microemulsions, micelles, sponge phase and the like. By "gel" it is meant a polymeric material having varying viscosities depending on the amount of polymer and diluent and can include liquids, pastes, gels, rubbers and the like.

Functional groups such as polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, or trialkoxysilyl groups, are present in the silicone elastomer composition. Such functional groups may be present in the silicone elastomer composition by blending into the elastomer a compound containing the functional group, using a diluent that contains the functional group, using a siloxane (I) and/or crosslinker (II) that contains the functional group and/or reacting the functional group into the silicone elastomer composition.

Component (I) is a siloxane oligomer or polymer having units of

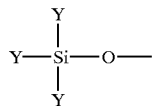

where Y independently is $R^{40}$ is selected from the group consisting of an alkyl group with 1 to 30 C atoms, an aryl group having 6 to 15 carbon atoms, an alkaryl group having 6 to 15 carbon atoms, and an aralkyl group having 6 to 15 carbon atoms;

Z is selected from epoxy functional groups, chlorohydrin functional groups, or mixtures thereof Z' is a functional group that react with epoxy groups or chlorohydrin functional groups (i.e. amine, hydroxyl), F is a functional groups other than Z or Z', and O (oxygen radicals);

with the with the proviso that at least 50 mol % of the Y groups in the siloxane are R', preferably methyl and there are at least two Z and/or Z' groups in the siloxane.

Siloxane (I) can be comprised of $Y_3SiO$-units, $Y_2SiO_{2/2}$-units, $YSiO_{3/2}$-units and $SiO_{4/2}$ units wherein Y is as defined above. Preferable siloxane (I) is primarily comprises of $Y_2SiO_{2/2}$-units.

R' groups may be exemplified by, but not limited to, methyl, ethyl, propyl, isopropyl, butyl, isobutyl, and phenyl, preferably methyl.

Z groups may be exemplified by, but not limited to epoxy groups and chlorohydrin groups and mixtures thereof.

Z' groups may be exemplified by, but not limited to, amine groups and hydroxyl groups.

F groups may be exemplified by, but not limited to, polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, trialkoxysilyl groups, the following functional groups wherein R is the same as R' defined above:

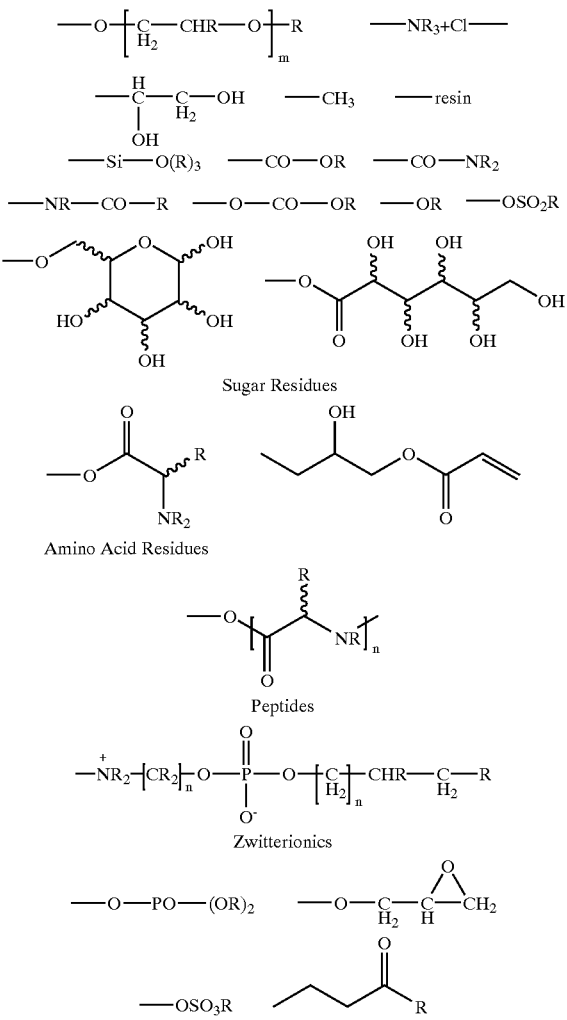

and mixtures thereof.

In Siloxane (I), there must be at least two reactive groups selected from Z and/or Z'. Preferably the reactive group is Z' and even more preferable the reactive group is an amine functional group.

Amine functional silicones that may be useful typically are of the formula

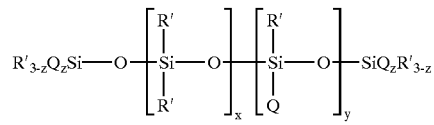

wherein R' is independently an alkyl group with 1 to 30 C atoms, an aryl group having 6 to 15 carbon atoms, an alkaryl group having 6 to 15 carbon atoms, and an aralkyl group having 6 to 15 carbon atoms with the proviso that at least 50% of the total number of R' groups are methyl; Q is an amine functional substituent of the formula —R"A wherein R" is a divalent alkylene radical having 3 to 6 carbons and A is a monovalent radical selected from the group consisting of —NR'", and —NR'"(CH$_2$)$_b$NR$_2$'"; wherein R'" denotes hydrogen or an alkyl group having 1 to 4 carbons, and b is a positive integer having a value of from 2 to 6; z has a value of 0 to 1; x has an average value of 5 to 3000; y has an average value of 0 to 3000 when z is 1, and y has an average value of 1 to 3000 when z is 0.

R" groups may be exemplified by, but not limited to, trimethylene, tetramethylene, pentamethylene, —CH$_2$CH (CH$_3$)CH$_2$—, and —CH$_2$CH$_2$CH(CH$_3$)CH$_2$— radicals. Preferable R' is a trimethylene or an alkyl substituted trimethylene radical such as —CH$_2$CH(CH$_3$)CH$_2$—.

R'" groups may be exemplified by, but not limited to methyl, ethyl, propyl, isoproplyl, butyl, and isobutyl.

A may be exemplified by, but not limited to, —NH$_2$, alkyl substituted amine radicals such as —NHCH$_3$, and —NHCH$_2$CH$_2$CH$_2$CH$_3$; and aminoalkyl substituted amine radicals such as —NHCH$_2$CH$_2$NH$_2$, —NH(CH$_2$)$_6$NH$_2$ and —NHCH$_2$CH$_2$CH$_2$N(CH$_3$)$_2$.

In the above amine functional silicone formula when z is 0, the silicon has only pendent amine functional substituents; when z is 1, the amine functional substituents may be terminal or both terminal and pendant. In the above amine functional silicone, x is preferably from about 5 to 500 and y is preferably from 0 to 100 when z is 1 and from 1 to 100 when z is 0. Most preferably, x+y is in the range of about 15 to 1000.

The amine content (the number of amine functional groups in the molecule of the amine functional silicone) is generally expressed as mole percent amine. Mole percent amine is determined according to the relationship y/DP× 100, where y is the value of integer y in the above formula for the amine functional silicone and DP (Degree of Polymerization) is x+y+2 which indicates the chain length of the amine functional silicone.

Amine functional silicones useful herein are well known in the art and are commercially available.

Siloxane (I) may also be an epoxy functional silicone. Epoxy functional silicones of the general structure shown below can be used, in which subscript a represents an integer of one or more.

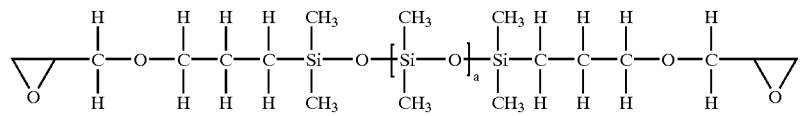

Epoxy functional silicones are well known in the art and available commercially. Such silicones have a viscosity ranging from 1 to about 200 centistoke (mm$^2$/s) and molecular weights of about 300–6,000.

The crosslinker (II) can be organic compounds such as organic amines, organic epoxides or siloxanes of the general formula provided for siloxane (I), above. The amount of crosslinker (II) will depend on the amount of reactive sites in the either Z and/or Z' groups in siloxane (I) and the molecular weight of siloxane (I) (i.e. —NHCH$_2$CH(CH$_3$) CH$_2$NHCH$_2$CH$_2$NH$_2$ groups contains three reactive sites). One skilled in the art will be able to readily calculate the amount of crosslinker needed to ensure partial or complete reaction between the Z and Z' groups. Typically the ratio of reactive sites in the Z to Z' groups is from 0.1:1 to 1.5:1, preferably 0.2:1 to 0.5:1, more preferably 0.25:1 to 0.35:1.

Organic epoxides containing at least two epoxy groups suitable for use herein include ethylene glycol diglycidyl ether, diethylene glycol diglycidyl ether, polyethylene glycol diglycidyl ether, glycerine diglycidyl ether, triglycidyl ether, propylene glycol diglycidyl ether, and butanediol diglycidyl ether; 1,2,3,4-diepoxybutane; 1,2,4,5-diepoxypentane; 1,2, 5,6-diepoxyhexane; 1,2,7,8-diepoxyoctane; 1,3-divinylbenzene diepoxide; 1,4-divinylbenzene diepoxide; 4,4'-isopropylidene diphenol diglycidyl ether, and hydroquinone diglycidyl ether. Other polyglycidyl ethers of alkane polyols, polyglycidyl ethers of poly(alkylene glycols), diepoxy alkanes, diepoxy aralkanes, and polyphenol polyglycidyl ethers, can also be used herein. Alternatively chlorohydrins may be used in place of or in conjunction with the epoxides.

Two especially preferred organic epoxides containing at least two epoxy groups are shown below, in which n is a positive integer determining the molecular weight of the epoxide.

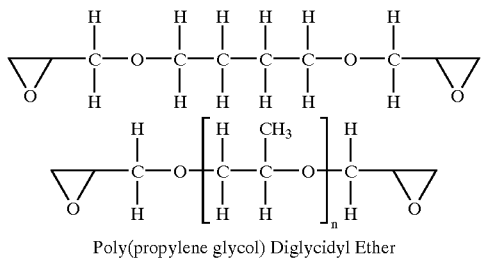

Poly(propylene glycol) Diglycidyl Ether

Organic amine compounds useful herein include ethane semicarbazole, acetaldehydeammonia, acetamide, dichloroacetamide, thioacetarnide, acetamidine, o-aminoacetophenone, acrylamide, adalin, adipamide, allanturic acid, ethyl ester of allophanic acid, allylamine, ammelide, tert-amylamine, aniline, n-benzohydryl, 2,4-dibromo-6-nitroaniline, o-ffuoroaniline, p-nitrosoaniline, ar-pentachloroaniline, pp'-thiodianiline, anisamide, m-anisidine, 9,10-anthradiamine, anthranilaldehyde, methyl ester of anthranilic acid, 3-nitroanthranilic acid, anthranilonitrile, 2-amino-1-hydroxyanthraquinone, arsanilic acid, L-aspartic acid, p-aminoazobenzene, 5,5 diallyl-barbituric acid, 5 (2 furfurylidene)-2 thiobarbituric acid, benzalhydrazine, benzamidoxime, benzamidine, benzenepentamine, benzenesulfonamide, 3 ethoxybenzidine, benzidine sulfone, benzocaine, p-aminobenzohydrol, benzohydrazide, 3-amino-5-nitrobenzoic acid, o-sulfamylbenzoic acid, 2,2'-diaminobenzophenone, biguanide, acetylbiuret, bornylamine, 2-aminobutanol, cadaverine, 3-aminocamphor, dithiocarbamic acid, thiolcarbamic acidethyl ester, thionocarbamic acidethyl ester, thiocarbanilide, 1,5-diphenylearbohydrazide, m-aminocinnamic acid, 3-amino-o-cresol, crotonamide, cyanamide, cyclohexylamine, L-cysteine, diethylenetriamine, ethoxyamine, formamide, formohydrazide, Dfructosamine, guanidine, p-bromophenylhydrazine, piperazine, o-nitrophenylhydrazine, lactamide, nicotinamide, ethyloxamate, oxamide, pararosaniline, 2-phenanthrylamine, 2 nitrophenetidine, p-aminothiophenol, 2-aminopyridine, 4-aminoquinoline, thiosemicarbazide, sulfanilamine, tetradecylamine, 3-thiophenesulfonamide, thiophenine, aaa-trifluoro-m-toluidine, 2-bromo-5-nitro-ptoluidine, urea, allylurea, allylthiourea, ethylideneurea, nitrourea, p-phenethylurea, vinylamine, sulfaguanidine, dimethylgallium amide, and aminophenylmercuric acetate.

Preferably the organic amine is selected from ammonia, diethylene triamine, ethylene diamine, methane diamine, m-phenylene diamine, methylene dianiline, benzohydrazide, guanidine, benzidene sulfone, thioacetamide, piperazine, p-amino benzoic acid, thiosemicarbizide, allanturic acid, p,p'-thiodianiline, p-bromophenyl hydrazine, benzene pentamine, and N,N'-dimethyl ethylene diamine If desired, crosslinkers (II) that contain a single Z or Z' group can be included as an additional component, in order to control the cross link density and the overall molecular weight of the silicone elastomer.

The reaction between siloxane (I) and crosslinker (II) is carried out in the presence of a diluent (III) selected from (i) water, (ii) a silicone fluid; (iii) a polar organic compound, (iv) a non-polar organic compound and (iv) mixtures thereof. Typically the diluent is present in an amount of 0.1 to 99.89 wt. % based on the weight of all components. Preferably the diluent (III) is present in an amount of from 1 to 80 wt. % and more preferably from 1 to 50 wt. %. When the diluent is a polar organic compound or non-polar organic compound an amount should be used to create a product containing <40 wt. % solids.

The diluent is an integral part of the resulting elastomer composition and affects the structural and physical properties of the silicone elastomer. Preferably the diluent is not removed from the silicone elastomer composition.

When water (III)(i) is used as the solvent the resulting silicone elastomer can be in the form of a silicone gel or organized structure.

Silicone fluids (II)(ii) useful as the solvent include, but are not limited to alkyl and/or aryl siloxanes such as methyl siloxanes and alkyl and/or aryl siloxanes containing functional groups wherein the functional groups do not react with or substantially change the reaction between Z and Z'. Preferred are volatile methyl siloxanes (VMS). VMS compounds correspond to the average unit formula $(CH_3)_jSiO_{(4-j)/2}$ in which j has an average value of 2 to 3. The VMS compounds contain siloxane units joined by Si—O—Si bonds. Representative siloxane units are monofunctional "M" units: $(CH_3)_3SiO_{1/2}$ and difunctional "D" units: $(CH_3)_2SiO_{2/2}$. The presence of trifunctional "T" units: $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH_3)_3SiO\{(CH_3)_2SiO\}_k Si(CH_3)_3$ where k is 0–5. Cyclic VMS have the formula $\{(CH_3)_2SiO\}m$ where m is 3–9. Preferably, these volatile methyl siloxane have a normal boiling point less than about 250° C. and viscosity of about 0.65 to about 5.0 mm²/s.

Representative linear volatile methyl siloxanes include, but are not limited to, hexamethyldisiloxane, octamethyltrisiloxane, decamethyltetrasiloxane, dodecamethylpentasiloxane, tetradecamethylhexasiloxane, and hexadecamethylheptasiloxane. Representative cyclic volatile methyl siloxanes are hexamethylcyclotrisiloxane; octamethylcyclotetrasiloxane, decamethylcyclopentasiloxane; and dodecamethylcyclohexasiloxane.

Representative branched volatile methyl siloxanes are heptamethyl-3-{(trimethylsilyl)oxy}trisiloxane, hexamethyl-3,3 ,bis{(trimethylsilyl)oxy}trisiloxane, and pentamethyl{(trimethylsilyl)oxy}cyclotrisiloxane.

The silicone fluid (III)(ii) useful herein also includes using silicone fluids represented respectively by formulas $R_3SiO(R_2SiO)_nSiR_3$ and $(R_2SiO)_p$ wherein R is as defined above. The value of subscript n is 0–80, preferably 5–20. The value of subscript p is 3–9, preferably 4–6. These polysiloxanes have a viscosity generally in the range of about 1–100 mm²/polymers with a viscosity in the range of about 100–1,000 mm²/sec. Typically, n can be about 80–375. Illustrative of such silicone fluids are polydimethylsiloxane, polydiethylsiloxane, polymethylethylsiloxane, polymethylphenylsiloxane, and polydiphenylsiloxane.

Functional silicone fluids can also be employed as the diluent (III). Useful functional silicone fluids are represented by the formula $R_3SiO(RFSiO)nSiR_3$ where F is a functional group as defined above. Examples of functional silicone fluids include, but are not limited to, are acrylamide functional siloxane fluids, acrylate functional siloxane fluids, carbinol functional siloxane fluids, carboxy functional siloxane fluids, chloroalkyl functional siloxane fluids, glycol functional siloxane fluids, ketal functional siloxane fluids, mercapto functional siloxane fluids, methyl ester functional siloxane fluids, perfluoro functional siloxane fluids, polyisobutylene (PIB) functional siloxane fluids, silanol functional siloxanes, and vinyl functional siloxane fluids.

Silicone fluids (III)(ii) are exemplified in U.S. Pat. No. 5,948,855 issued Sep. 7, 1999, incorporated herein for its teaching of silicone fluids.

When silicone fluids are used as the diluent herein, the resulting silicone elastomer is in the form of silicone gels.

Polar organic compounds (III)(iii) may also be used as the diluent. Polar organic compounds useful herein include monohydroxy alcohols such as ethyl alcohol and isopropyl alcohol; diols and triols such as propylene glycol, 2-methyl-1,3-propane diol $HOCH_2CH(CH_3)CH_2OH$, 1,2-hexanediol $CH_3(CH_2)_3CH(OH)CH_2OH$, and glycerol; glycerol esters such as glyceryl triacetate (triacetin), glyceryl tripropionate (tripropionin), and glyceryl tributyrate (tributyrin); and polyglycols such as polyethylene glycols and polypropylene glycols, among which are PPG-14 butyl ether $C_4H_9[OCH(CH_3)CH_2]_{14}OH$.

Non-polar organic compounds (III)(iv) may also be used as the diluent. The non-polar organic compounds include aromatic hydrocarbons, aliphatic hydrocarbons, alcohols, aldehydes, ketones, amines, esters, ethers, glycols, glycol ethers, alkyl halides, or aromatic halides. Representative compounds are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Maker's & Painter's (VM&P) solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, benzyl acetate, and isopropyl palmitate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as petroleum jelly, mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

Non-polar organic compounds are described in U.S. Pat. No. 5,948,855 issued Sep. 7, 1999, herein incorporated by reference for its teaching of non-polar organic compounds.

In particular the non-polar organic compounds can be fragrances, natural oils derived from animal, vegetable or mineral sources. Most preferred are cosmetic oils such as almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

When a polar or non-polar organic solvent is used the resulting silicone elastomer is in the form of a silicone gel. When a polar organic solvent is used the resulting silicone elastomer may also be in the form of an organized structure.

Optionally, there may be present (IV) a surfactant. The surfactants are typically present in the amount of 1 to 80 wt. % based on the total composition. Preferably the surfactant is present in the amount of 1 to 50 wt. % based on the total composition and more preferably in the amount of 1 to 30 wt. %. The surfactant can be a nonionic, cationic, anionic, or a mixture of such surfactants. Most preferred are organic nonionic surfactants, but the nonionic surfactant can be one containing silicon atoms. Most preferred are alcohol ethoxylates $R^2$—$(OCH_2CH_2)_cOH$, most particularly fatty alcohol ethoxylates. Fatty alcohol ethoxylates typically contain the characteristic group —$(OCH_2CH_2)_cOH$ which is attached to fatty hydrocarbon residue R which contains about eight to about twenty carbon atoms, such as lauryl ($C_{12}$), cetyl ($C_{16}$) and stearyl ($C_{18}$). While the value of "c" may range from 1 to about 100, its value is typically in the range of 2 to 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under such names as ALFONIC®, BRIJ, GENAPOL®, LUTENSOL, NEODOL®, RENEX, SOFTANOL, SURFONIC®, TERGITOL®, TRYCOL, and VOLPO.

One especially useful nonionic surfactant is polyoxyethylene (23) lauryl ether, a product sold under the name BRIJ 35L by ICI Surfactants, Wilmington, Del. It has an HLB of about 16.9

Cationic surfactants useful in the invention include compounds containing quaternary ammonium hydrophilic moieties in the molecule which are positively charged, such as quaternary ammonium salts represented by $R^3R^4R^5R^6N^+X^-$ where $R^3$ to $R^6$ are alkyl groups containing 1–30 carbon atoms, or alkyl groups derived from tallow, coconut oil, or soy; and X is halogen such as chlorine or bromine, or X can be a methosulfate group. Most preferred are dialkyldimethyl ammonium salts represented by $R^7R^8N^+(CH_3)_2X^-$, where $R^7$ and $R^8$ are alkyl groups containing 12–30 carbon atoms, or alkyl groups derived from tallow, coconut oil, or soy; and X is halogen or a methosulfate group. Monoalkyltrimethyl ammonium salts can also be employed, and are represented by $R^9N^+(CH_3)_3X^-$ where R is an alkyl group containing 12–30 carbon atoms, or an alkyl group derived from tallow, coconut oil, or soy; and X is halogen or a methosulfate group.

Representative quaternary ammonium salts are dodecyltrimethyl ammonium bromide (DTAB), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under such names as ADOGEN, ARQUAD, SERVAMINE, TOMAH, and VARIQUAT.

Examples of anionic surfactants include sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate $CH_3(CH_2)_{11}OSO_3Na$; ether sulfates having alkyl groups of eight or more carbon atoms; and alkylaryl sulfonates having one or more alkyl groups of eight or more carbon atoms.

Commercial anionic surfactants useful in this invention include triethanolamine linear alkyl sulfonate sold under the name BIO-SOFT N-300 by the Stepan Company, Northfield, Ill.; sulfates sold under the name POLYSTEP by the Stepan Company; and sodium n-hexadecyl diphenyloxide disulfonate sold under the name DOWFAX 8390 by The Dow Chemical Company, Midland, Mich.

Optionally, there may be present (V) an active ingredient. Active ingredients useful herein include, but are not limited to fragrances, sunscreens (i.e. a UV absorber/UV light stabilizer) vitamins, drugs including activated antiperspirant salts such as aluminum chlorohydrate and aluminum-zirconium trichlorohydrate, and α-hydroxy acids such as glycolic acid, lactic acid, tartaric acid, and citric acid, i.e.,fruit acids. Vitamins and drugs which can be used are described in U.S. Pat. No. 5,948,855, herein incorporated by reference for its teaching of these actives. These active ingredients may be further exemplified by vitamin C, vitamin $B_1$, vitamin $B_2$, vitamin $B_6$, vitamin $B_{12}$, niacin, folic acid, biotin, and pantothenic acid.

Fragrances may be exemplified by, but not limited to, perfume ketones and perfume aldehydes.

Preferably the perfume ketone is selected for its odor character from buccoxime; iso jasmone; methyl beta naphthyl ketone; musk indanone; tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-lonone, Beta-lonone, Gamma-Methyl so-called lonone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyldecahydro-2-naphtone, Dimethyl-Octenone, Freskomenthe, 4-(1-Ethoxyvinyl)-3,3,5,5,-tetramethyl-Cyclohexanone, Methyl-Heptenone, 2-(2-(4-Methyl-3-cyclohexen-1-yl)propyl)-cyclopentanone, 1-(p-Menthen-6 (2)-yl)-1-propanone, 4-(4-Hydroxy-3-methoxyphenyl)-2-butanone, 2-Acetyl-3,3-Dimethyl-Norbomane, 6,7-

Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran.

More preferably, the perfume ketones are selected for its odor character from Alpha Damascone, Delta Damascone, Iso Damascone, Carvone, Gamma-Methyl-lonone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal; anisic aldehyde; cymal; ethyl vanillin; florhydral; helional; heliotropin; hydroxycitronellal; koavone; lauric aldehyde; lyral; methyl nonyl acetaldehyde; P. T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy] acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexancarboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carbox aldehyde, 5 or 6 methoxy0hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena 1, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl)benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde and mixtures thereof.

More preferred aldehydes are selected for its odor character from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof.

In the above list of perfume ingredients, some are commercial names conventionally known to one skilled in the art, and also includes isomers. Such isomers are also suitable for use in the present invention.

Other active ingredients which can be carried in a phase (s) of the silicone fluid or nonpolar organic compound include, but are not limited to vitamins and drugs among which are vitamin A, RETINOL, $C_2$–$C_{18}$ esters of RETINOL, vitamin E, tocopherol, esters of vitamin E, retinyl acetate, retinyl palmitate, retinyl propionate, α-tocopherol, tocophersolan, tocopheryl acetate, tocopheryl linoleate, tocopheryl nicotinate, tocopheryl succinate, and mixtures thereof. These active ingredients are described in U.S. Pat. No. 5,948,855, herein incorporated by reference for its teaching of these actives.

Optionally, there may be present a compound (VI) that introduces functional groups, F, into the silicone elastomer ("functional compound") wherein F is as described above. The functional compound may be silicone, organic. It may be reactive with the siloxane (I) and/or crosslinker (II) resulting in functionality that is bonded directly to the silicone elastomer. It may be unreactive resulting in functionality that is in the silicone elastomer composition. The functional compound can be added before, during or after the crosslinking reaction. Combinations of functional compounds can be used or combinations of functionality may be used so long as the functional compound does not substantially interfere with the crosslinking chemistry.

The silicone elastomer compositions are prepared by combining the siloxane (1), crosslinker (II) and diluent (III). No special equipment or processing conditions are generally required. Heat and agitation may be applied to facilitate the crosslinking reaction. Typically, the reaction mixture is heated to 25 to 100° C. Simple propeller mixers, turbine-type mixers, Brookfield counter-rotating mixers, or homogenizing mixers may be used. Often, simple hand shaking is sufficient. Optional components and additional diluents may be added before, during or after the crosslinking reaction has taken place.

When using water and/or a polar organic solvent as the diluent it is preferred to carry out the reaction as an emulsion polymerization. Emulsion polymerization is well known in the art however, it typically entails simultaneous polymerization and emulsification wherein the resulting silicone elastomer composition is in the form of an emulsion, preferably a microemulsion.

Typically, the diluent is not removed from the silicone elastomer composition. However, it is possible to remove the diluent using techniques known in the art, for example, spray drying to produce a solid-like particle. The silicone elastomer may then be used in the solid-like form or it may be re-swelled in the same or a different diluent.

One of the benefits derived from silicone elastomer compositions prepared according to this invention is their structural integrity against changes in such parameters as temperature, and the presence or absence of other components such as water, surfactants, and oils. Another benefit is their reduced permeability for entrapped active ingredients by the formation of crosslinked structures.

The silicone elastomer compositions are useful in personal care products, for example, in preparing antiperspirants and deodorants. They can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. They can be used in hair shampoos, hair conditioners, hair sprays, mousses, permanents, depilatories, and cuticle coats. In cosmetics they can be added to make-ups, color cosmetics, foundations, blushes, lipsticks, eyeliners, mascara, oil removers, color cosmetic removers, and powders. In such applications the compositions may include oil soluble, polar solvent soluble, and water-soluble ingredients such as vitamins as noted above.

These compositions are also capable of functioning as carriers for pharmaceuticals, biocides, herbicides, pesticides, and other biologically active substances; and they have utility as additives for cellulosic or synthetic nonwoven carrier substrates used in wet-like cleansing wipes such as wet-wipes, tissues, and towels, marketed generally for personal hygiene and household cleaning tasks.

EXAMPLES

The following non-limiting examples are provided so that one skilled in the art may more readily understand the invention.

Example 1

Into a reaction vessel was placed 57 g of an amino siloxane (DP=323, 2.7 mole percent isobutyl ethylene diamine methyl siloxane groups). The compound was heated to 50°±5° C. and then 1.5 g of glycidol was added slowly and the temperature was raised to 75°±5° C. and maintained for 1 hour. At this time the mixture was cooled to room temperature to yield a cloudy white viscous oil. 4.0 g of this material was placed in a vial with 16.0 g of decamethylcyclopentasiloxane and 0.14 g of 1,4-butanediol diglycidyl ether. This mixture was heated to 70°±5° C. for 48 hours and yielded a cloudy gel.

Example 2

Into a vial was placed 3.5 g of an amino siloxane (DP=97, 2.0 mole percent isobutyl ethylene diamine methyl siloxane groups, where 16 mole percent of the amine sites have been modified with 3-dodecyldimethylammonium-2-hydroxypropyl groups) and 16 g of decamethylcyclopentasiloxane with 0.5 g of 1,4-butanediol diglycidyl ether. The mixture was heated to and maintained at 70±5° C. for 48 hours and a clear firm gel was obtained.

Example 3

Into a vial was placed 3.5 g of an amino siloxane (DP=97, 2.0 mole percent isobutyl ethylene diamine methyl siloxane groups, where 16 mole percent of the amine sites have been modified with 3-dodecyldimethylammonium-2-hydroxypropyl groups) and 16 g of decamethylcyclopentasiloxane with 0.5 g of trimethylolpropane triacrylate. The mixture was heated to 70±5° C. for 15 hours and a clear firm gel was obtained.

Example 4

In a flask was placed 203 g of an amino siloxane (DP=323, 2.7 mole percent isobutyl ethylene diamine methyl siloxane groups) and 9.4 g of allyl methacrylate. This mixture was heated to and maintained at 85°±15° C. for 6 hours. Approximately, 3.5 g of this material was placed in a vial with 16 g of decamethylcyclopentasiloxane and 0.5 g of trimethylolpropane triacrylate. This mixture was heated to and maintained at 70°±5° C. for 15 hours and a clear firm gel was obtained.

Example 5

Into a vial was placed 3.5 g of an amino siloxane (DP=97, 2.0 mole percent isobutyl ethylene diamine methyl siloxane groups, where 25 mole percent of the amine sites have been modified by reaction with glycidol) and 16 g of decamethylcyclopentasiloxane with 0.5 g of trimethylolpropane triacrylate. The mixture was heated to and maintained at 70°±5° C. for 15 hours and a clear firm gel was obtained.

Example 6

Into a vial was placed 3.5 g of an amino siloxane (DP=97, 2.0 mole percent isobutyl ethylene diamine methyl siloxane groups, where 25 mole percent of the amine sites have been modified by reaction with glycidol) and 16 g of decamethylcyclopentasiloxane with 0.5 g of glycidyl methacrylate. The mixture was heated to and maintained at 70°±5° C. for 24 hours and a clear firm gel was obtained.

Example 7

Into a vial was placed 3.5 g of an amino siloxane (DP=97, 2.0 mole percent isobutyl ethylene diamine methyl siloxane groups, where 10 mole percent of the amine sites have been modified by reaction with an epoxy capped polyether ($EO_7$)) and 16 g of decamethylcyclopentasiloxane with 0.5 g of 1,4-butanediol diglycidyl ether. The mixture was heated to and maintained at 70°±5° C. for 48 hours and a clear gel was obtained.

Example 8

Into a vial was placed 3.5 g of an amino siloxane (DP=97, 2.0 mole percent isobutyl ethylene diamine methyl siloxane groups, where 10 mole percent of the amine sites have been modified by reaction with an epoxy capped polyether ($EO_7$)) and 16 g of decamethylcylopentasiloxane with 0.5 g of trimethylolpropane triacrylate. The mixture was heated to and maintained at 70°±5°C. for 15 hours and a clear firm gel was obtained.

What is claimed is:

1. A silicone elastomer in the form of a gel and/or organized structure produced by reacting (I) 0.1 to 99.89 wt. % based on the weight of all components of a siloxane oligomer or polymer having units of

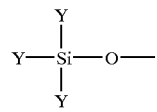

where each Y is independently selected from divalent oxygen atoms

R': an alkyl group with 1 to 30 C atoms, an aryl group having 6 to 15 carbon atoms, an alkaryl group having 6 to 15 carbon atoms, and an aralkyl group having 6 to 15 carbon atoms;

Z: a reactive group selected from epoxy functional groups or chlorohydrin functional groups;

Z': a functional group that reacts with epoxy-functional groups or chlorohydrin functional groups;

F: a functional group selected from polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, and trialkoxysilyl groups;

with the proviso that at least 50 mol % of the Y groups in the siloxane are R' and there are at least two Z and/or Z' groups in the siloxane; and (II) 0.1 to 99.89 wt. % based on the weight of all components of a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both, further wherein (I), (II) or both (I) and (II) contain at least one F group; with the additional proviso that F and Z and/or Z' are different in (III) 0.1 to 99.89 wt. % based on the weight of all components a diluent selected from (i) water; (ii) a silicone fluid; (iii) a polar organic compound and mixtures thereof.

2. The silicone elastomer as claimed in claim 1 wherein in siloxane (I) there are at least two Z' groups and the crosslinker (II) contains Z groups.

3. The silicone elastomer as claimed in claim 1 wherein in siloxane (I) there are at least two Z groups and the crosslinker contains (II) Z' groups.

4. The silicone elastomer as claimed in claim 1 wherein siloxane (I) contains at least one F group.

5. The silicone elastomer as claimed in 2 wherein siloxane (I) contains at least one F group.

6. The silicone elastomer as claimed in claim 3 wherein siloxane (I) contains at least one F group.

7. The silicone elastomer as claimed in claim 1 wherein R' is a methyl group.

8. The silicone elastomer as claimed in claim 2 wherein the Z' group is an amine group and Z is an epoxy-functional group.

9. The silicone elastomer as claimed in claim 3 wherein Z is an epoxy-functional group and Z' is an amine group.

10. The silicone elastomer as claimed in claim 1 wherein the diluent is water.

11. The silicone elastomer as claimed in claim 1 wherein the diluent is a silicone fluid.

12. The silicone elastomer as claimed in claim 1 wherein the diluent is a polar organic compound.

13. The silicone elastomer as claimed in claim 1 wherein the elastomer is in the form of a gel.

14. The silicone elastomer as claimed in claim 1 wherein the elastomer is in the form of an organized structure.

15. The silicone elastomer as claimed in claim 1 wherein there is additionally present (IV) 1 to 80 wt % of a surfactant.

16. The silicone elastomer as claimed in claim 1 wherein there is additionally present (V) an active ingredient.

17. A silicone elastomer in the form of a gel and/or organized structure produced by reacting (I) 0.1 to 99.89 wt. % based on the weight of all components of a siloxane oligomer or polymer having units of

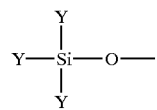

where each Y is independently selected from divalent oxygen atoms

R': an alkyl group with 1 to 30 C atoms, an aryl group having 6 to 15 carbon atoms, an alkaryl group having 6 to 15 carbon atoms, and an aralkyl group having 6 to 15 carbon atoms;

Z: a reactive group selected from epoxy-functional groups or chlorohydrin functional groups;

Z': a functional group that reacts with epoxy-functional groups or chlorohydrin functional groups;

F: a functional groups selected from polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, and trialkoxsilyl groups;

with the proviso that at least 50 mol % of the Y groups in the siloxane are R' and there are at least two Z and/or Z' groups in the siloxane; and (II) 0.1 to 99.89 wt. % based on the weight of all components of a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both, in (III) 0.1 to 99.89 wt. % based on the weight of all components a functional silicone fluid.

18. A silicone elastomer in the form of a gel and/or organized structure produced by (A) reacting (I) 0.1 to 99.89 wt. % based on the weight of all components of a siloxane oligomer or polymer having units of

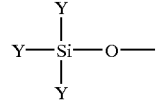

where each Y is independently selected from divalent oxygen atoms

R': an alkyl group with 1 to 30 C atoms, an aryl group having 6 to 15 carbon atoms, an alkaryl group having 6 to 15 carbon atoms, and an aralkyl group having 6 to 15 carbon atoms;

Z: a reactive group selected from epoxy-functional groups or chlorohydrin functional groups;

Z': a functional group that reacts with epoxy-functional groups or chlorohydrin functional groups;

with the proviso that at least 50 mol % of the Y groups in the siloxane are R' and there are at least two Z and/or Z' groups in the siloxane; and (II) 0.1 to 99.89 wt. % based on the weight of all components of a crosslinker wherein said crosslinker contains Z and/or Z' groups with the proviso that when Y in siloxane (I) contains Z groups, the crosslinker contains Z' groups; when Y in siloxane (I) contains Z' groups, the crosslinker contains Z groups; and when Y in siloxane (I) contains Z and Z' groups, the crosslinker contains Z groups, Z' groups or both, in (III) 0.1 to 99.89 wt. % based on the weight of all components a diluent selected from (i) water; (ii) a silicone fluid; (iii) a polar organic compound and (iv) a non-polar organic compound and (v) mixtures thereof;

(B) further reacting the product produced in (A) with a compound containing functional group F wherein F is selected from polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, and trialkoxysilyl groups.

19. A silicone elastomer in the form of a gel and/or organized structure produced by (A) reacting (I) 0.1 to 99.89 wt. % based on the weight of all components of a siloxane oligomer or polymer having units of

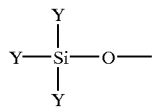

where each Y is independently selected from divalent oxygen atoms

R': an alkyl group with 1 to 30 C atoms, an aryl group having 6 to 15 carbon atoms, an alkaryl group having 6 to 15 carbon atoms, and an aralkyl group having 6 to 15 carbon atoms;

Z: a reactive group selected from epoxy functional groups or chlorohydrin functional groups;

Z': a functional group that reacts with epoxy groups or chlorohydrin functional groups; with the proviso that at least 50 mol % of the Y groups in the siloxane are R' and there are at least two Z and/or Z' groups in the siloxane; and (II) 0.1 to 99.89 wt. % based on the weight of all components of a crosslinker wherein said crosslinker contains Z and/or Z' groups with the proviso that when Y in siloxane (I) contains Z groups, the crosslinker contains Z' groups: when Y in siloxane (I) contains Z' groups, the crosslinker contains Z groups: and when Y in siloxane (I) contains Z and Z' groups, the crosslinker contains Z groups, Z' groups or both, (III) a compound containing a functional group F wherein F is selected from polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, and trialkoxysilyl groups.

in (IV) 0.1 to 99.89 wt. % based on the weight of all components a diluent selected from (i) water; (ii) a silicone fluid; (iii) a polar organic compound and (iv) a non-polar organic compound and (v) mixtures thereof.

20. A silicone elastomer in the form of a gel and/or organized structure produced by reacting (I) 0.1 to 99.89 wt. % based on the weight of all components of a siloxane oligomer or polymer having units of

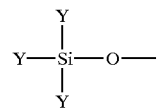

where each Y is independently selected from

R': an alkyl group with 1 to 30 C atoms, an aryl group having 6 to 15 carbon atoms, an alkaryl group having 6 to 15 carbon atoms, and an aralkyl group having 6 to 15 carbon atoms;

Z': a functional group that reacts with epoxy-functional groups or chlorohydrin functional groups;

F: a functional group selected from polyether groups, quaternary ammonium salt groups, monohydroxy alcohol groups, polyhydroxy alcohol groups, carbohydrate groups, acrylate groups, ester groups, amide groups, carbonate groups, carboxylate groups, sulfonate groups, sulfate groups, halogen groups, and trialkoxysilyl groups; with the proviso that at least 50 mol % of the Y groups in the siloxane are R' and there are at least two Z' groups at least one F group in the siloxane; and (II) 0.1 to 99.89 wt. % based on the weight of all components of a crosslinker wherein said crosslinker is an organic compound containing Z groups having a reactive group selected from epoxy-functional groups or chlorohydrin functional groups; in (III) 0.1 to 99.89 wt. % based on the weight of all components a diluent selected from (i) water; (ii) a silicone fluid; (iii) a polar organic compound and (iv) a non-polar organic compound and (v) mixtures thereof.

* * * * *